(12) United States Patent
Palti

(10) Patent No.: US 7,684,840 B2
(45) Date of Patent: Mar. 23, 2010

(54) SYSTEM AND METHOD FOR IN-VIVO SAMPLING AND ANALYSIS

(75) Inventor: Yoram Palti, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 1051 days.

(21) Appl. No.: 10/524,553

(22) PCT Filed: Aug. 7, 2003

(86) PCT No.: PCT/IL03/00651

§ 371 (c)(1),
(2), (4) Date: Oct. 11, 2005

(87) PCT Pub. No.: WO2004/014227

PCT Pub. Date: Feb. 19, 2004

(65) Prior Publication Data

US 2006/0106316 A1 May 18, 2006

Related U.S. Application Data

(60) Provisional application No. 60/402,703, filed on Aug. 13, 2002.

(51) Int. Cl.
*A61B 5/1455* (2006.01)
(52) U.S. Cl. ........................... 600/310; 600/476
(58) Field of Classification Search ........... 600/309–344
See application file for complete search history.

(56) References Cited

U.S. PATENT DOCUMENTS

| 3,683,389 A | 8/1972 | Hollis |
| 3,683,890 A | 8/1972 | Beal |
| 3,971,362 A | 7/1976 | Pope et al. |
| 4,017,261 A | 4/1977 | Svoboda et al. |
| 4,038,485 A | 7/1977 | Johnston et al. |
| 4,178,735 A | 12/1979 | Jackson |
| 4,239,040 A | 12/1980 | Hosoya et al. |
| 4,262,632 A | 4/1981 | Hanton et al. |
| 4,306,877 A | 12/1981 | Lubbers |
| 4,439,197 A | 3/1984 | Honda et al. |
| 4,646,724 A | 3/1987 | Sato et al. |
| 4,689,621 A | 8/1987 | Kleinberg |
| 4,741,327 A | 5/1988 | Yabe |

(Continued)

FOREIGN PATENT DOCUMENTS

DE  2929429  2/1980

(Continued)

OTHER PUBLICATIONS

U.S. Appl. No. 60/297,761, filed Jun. 14, 2001, Lewkowicz et al.

(Continued)

*Primary Examiner*—Eric F Winakur
(74) *Attorney, Agent, or Firm*—Pearl Cohen Zedek Latzer, LLP

(57) ABSTRACT

A system for in vivo analysis which includes agglutinative particles capable of interacting with at least one analyte so as to cause an optical change; and at least one in vivo imaging system (220, 230, 240) configured for detecting the optical change in vivo. The system may be incorporated within an ingestible capsule (100).

17 Claims, 3 Drawing Sheets

U.S. PATENT DOCUMENTS

| | | |
|---|---|---|
| 4,803,992 A | 2/1989 | Lemelson |
| 4,817,632 A | 4/1989 | Schramm |
| 4,819,620 A | 4/1989 | Okutsu |
| 4,844,076 A | 7/1989 | Lesho et al. |
| 4,885,077 A | 12/1989 | Karakelle et al. |
| 4,920,045 A | 4/1990 | Okuda et al. |
| 4,940,997 A | 7/1990 | Hamlin et al. |
| 5,006,314 A | 4/1991 | Gourley et al. |
| 5,042,486 A | 8/1991 | Pfeiler et al. |
| 5,081,040 A | 1/1992 | Patel et al. |
| 5,081,041 A | 1/1992 | Yafuso et al. |
| 5,088,492 A | 2/1992 | Takayama et al. |
| 5,096,671 A | 3/1992 | Kane et al. |
| 5,109,870 A | 5/1992 | Silny et al. |
| 5,114,864 A | 5/1992 | Walt |
| 5,187,572 A | 2/1993 | Nakamura et al. |
| 5,211,165 A | 5/1993 | Dumoulin et al. |
| 5,252,494 A | 10/1993 | Walt |
| 5,267,033 A | 11/1993 | Hoshino |
| 5,279,607 A | 1/1994 | Schentag et al. |
| 5,290,517 A | 3/1994 | Samuels et al. |
| 5,330,427 A | 7/1994 | Weissenburger |
| 5,362,478 A | 11/1994 | Desai et al. |
| 5,368,027 A | 11/1994 | Lubbers et al. |
| 5,376,336 A | 12/1994 | Lubbers et al. |
| 5,385,846 A | 1/1995 | Kuhn et al. |
| 5,395,366 A | 3/1995 | D'Andrea et al. |
| 5,398,670 A | 3/1995 | Ortiz et al. |
| 5,429,132 A | 7/1995 | Guy et al. |
| 5,443,701 A | 8/1995 | Willner et al. |
| 5,447,868 A | 9/1995 | Augurt |
| 5,460,969 A | 10/1995 | Fielder et al. |
| 5,479,935 A | 1/1996 | Essen-Moller |
| 5,490,969 A | 2/1996 | Bewlay et al. |
| 5,495,114 A | 2/1996 | Adair |
| 5,549,109 A | 8/1996 | Samson et al. |
| 5,558,640 A | 9/1996 | Pfeiler et al. |
| 5,563,071 A | 10/1996 | Augurt |
| 5,582,170 A | 12/1996 | Soller |
| 5,604,531 A | 2/1997 | Iddan et al. |
| 5,662,587 A | 9/1997 | Grundfest et al. |
| 5,762,770 A | 6/1998 | Pritchard et al. |
| 5,800,350 A | 9/1998 | Coppelson et al. |
| 5,814,525 A | 9/1998 | Renschler et al. |
| 5,819,736 A | 10/1998 | Avny et al. |
| 5,833,603 A | 11/1998 | Kovacs et al. |
| 5,837,196 A | 11/1998 | Pinkel et al. |
| 5,853,005 A | 12/1998 | Scanlon |
| 5,892,144 A | 4/1999 | Meller et al. |
| 5,913,820 A | 6/1999 | Bladen et al. |
| 5,929,901 A | 7/1999 | Adair et al. |
| 5,932,480 A | 8/1999 | Maruo et al. |
| 5,968,765 A | 10/1999 | Grage et al. |
| 5,986,693 A | 11/1999 | Adair et al. |
| 5,993,378 A | 11/1999 | Lemelson |
| 6,043,839 A | 3/2000 | Adair et al. |
| 6,074,349 A | 6/2000 | Crowley |
| 6,115,061 A | 9/2000 | Lieberman et al. |
| 6,162,171 A | 12/2000 | Ng et al. |
| 6,165,128 A | 12/2000 | C'espedes et al. |
| 6,174,291 B1 | 1/2001 | McMahon |
| 6,228,048 B1 | 5/2001 | Robbins |
| 6,233,476 B1 | 5/2001 | Stormmer et al. |
| 6,256,255 B1 | 7/2001 | Keeth et al. |
| 6,256,522 B1 | 7/2001 | Schultz |
| 6,285,897 B1 | 9/2001 | Kilcoyne et al. |
| 6,324,418 B1 | 11/2001 | Crowley et al. |
| 6,330,464 B1 | 12/2001 | Colvin, Jr. et al. |
| 6,330,465 B1 | 12/2001 | Huyberechts et al. |
| 6,369,812 B1 | 4/2002 | Lyriboz et al. |
| 6,395,562 B1 | 5/2002 | Hammock et al. |
| 6,400,980 B1 * | 6/2002 | Lemelson ............ 600/478 |
| 6,402,686 B1 | 6/2002 | Ouchi |
| 6,428,469 B1 * | 8/2002 | Iddan et al. ............ 600/109 |
| 6,475,145 B1 | 11/2002 | Baylor |
| 6,485,703 B1 * | 11/2002 | Cote et al. ............ 424/9.1 |
| 6,488,694 B1 | 12/2002 | Lau et al. |
| 6,498,941 B1 | 12/2002 | Jackson |
| 6,632,175 B1 | 10/2003 | Marshall |
| 6,692,430 B2 | 2/2004 | Adler |
| 6,709,387 B1 | 3/2004 | Glukhovsky et al. |
| 6,719,684 B2 | 4/2004 | Kim et al. |
| 6,936,003 B2 | 8/2005 | Iddan |
| 6,951,536 B2 * | 10/2005 | Yokoi et al. ............ 600/128 |
| 7,201,872 B2 | 4/2007 | Meron |
| 2001/0017649 A1 | 8/2001 | Yaron |
| 2001/0025135 A1 | 9/2001 | Naito et al. |
| 2001/0031502 A1 | 10/2001 | Watson, Jr. et al. |
| 2001/0034025 A1 | 10/2001 | Modlin et al. |
| 2001/0035902 A1 | 11/2001 | Iddan et al. |
| 2001/0051766 A1 | 12/2001 | Gazdzinski |
| 2001/0053535 A1 | 12/2001 | Bashir et al. |
| 2002/0015952 A1 | 2/2002 | Anderson et al. |
| 2002/0042562 A1 | 4/2002 | Meron et al. |
| 2002/0103417 A1 | 8/2002 | Gazdzinski |
| 2002/0111544 A1 | 8/2002 | Iddan |
| 2002/0127623 A1 * | 9/2002 | Minshull et al. ............ 435/7.92 |
| 2002/0146368 A1 | 10/2002 | Meron et al. |
| 2002/0158976 A1 | 10/2002 | Vni et al. |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0013370 A1 | 1/2003 | Glukhovsky |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0045790 A1 | 3/2003 | Lewkowicz et al. |
| 2003/0069474 A1 | 4/2003 | Couvillon, Jr. et al. |
| 2003/0114742 A1 | 6/2003 | Lewkowicz et al. |
| 2003/0139661 A1 | 7/2003 | Kimchy et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2004/0027459 A1 | 2/2004 | Segawa et al. |
| 2004/0073087 A1 | 4/2004 | Glukhovsky et al. |
| 2004/0176664 A1 | 9/2004 | Iddan |

FOREIGN PATENT DOCUMENTS

| | | |
|---|---|---|
| DE | 34 40 177 | 6/1986 |
| EP | 693271 | 1/1996 |
| EP | 945102 | 9/1999 |
| FR | 2 688 997 | 10/1993 |
| IL | 126727 | 10/1998 |
| IL | 143258 | 5/2001 |
| IL | 143259 | 5/2001 |
| JP | 57-45833 | 3/1982 |
| JP | 3-289779 | 12/1991 |
| JP | 4109927 | 4/1992 |
| JP | 4144533 | 5/1992 |
| JP | 4-180736 | 6/1992 |
| JP | 5015515 | 1/1993 |
| JP | 6063051 | 3/1994 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |

| | | |
|---|---|---|
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2002010990 | 1/2002 |
| JP | 2000342524 | 6/2002 |
| JP | 2000342525 | 6/2002 |
| WO | WO 92-21307 | 12/1992 |
| WO | WO 97-33513 | 9/1997 |
| WO | WO 98-11816 | 3/1998 |
| WO | WO 99-11754 | 3/1999 |
| WO | WO 99/32028 | 7/1999 |
| WO | WO 01/07919 | 2/2001 |
| WO | WO 01-08548 | 2/2001 |
| WO | WO 01-10291 | 2/2001 |
| WO | WO 01-25481 | 4/2001 |
| WO | WO 01/50941 | 7/2001 |
| WO | WO 01-53792 | 7/2001 |
| WO | WO 01-65995 | 9/2001 |
| WO | WO 01/69212 | 9/2001 |
| WO | WO 01-87377 | 11/2001 |
| WO | WO 02-26103 | 4/2002 |
| WO | WO 02-28910 | 4/2002 |
| WO | WO 02/055126 | 7/2002 |
| WO | WO 02/055984 | 7/2002 |
| WO | WO 02-067593 | 8/2002 |
| WO | WO 02/094337 | 11/2002 |
| WO | WO 03/003706 | 1/2003 |
| WO | WO 03/011103 | 2/2003 |
| WO | WO 2004/014227 | 2/2004 |
| WO | WO 2004/028336 | 4/2004 |
| WO | WO 2004/035106 | 4/2004 |
| WO | WO 2004/039233 | 5/2004 |

OTHER PUBLICATIONS

U.S. Appl. No. 09/807,892, filed Jun. 6, 2001, Meron et al.
U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 60/402,703, filed Aug. 13, 2002, Palti.
U.S. Appl. No. 60/421,788, filed Oct. 29, 2002, Iddan.
International Search Report for PCT/IL99/0554 dated Apr. 4, 2000.
Supplementary Partial European Search Report, Mar. 19, 2004.
International Search Report of PCT/IL02/00391, dated May 19, 2003.
Katgraber F, Glenewinkel F, Fischler S, Int J. Legal Med 1998; 111(3) 154-6.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
Evaluation of the heidelberg pH capsule: Method of Tubeless Gastric Analysis, Yarbrough, III et al., The American Journal Of Surgery, vol. 117, Feb. 1969, pp. 185-192.
Bio-Medical Telemetry: Sensing and Transmitting Biological Information from Animals and Man, R. Stuart Mackay, John Wiley and Sons, New York, 1970, pp. 244-245.
"The Heidelburg pH Capsule System Telemetric Fasting Gastric Analysis", Heidelburg International. Incorporated.
Heidelberger Kapsel—ein Kleinstsender fur die pH-Messung im Magen, Lange, et al., Telefunken-Zeitung, Jg 36 (1963) Heft 5, pp. 265-270.
"New Smart Plastic has Good Memory"—Turke, European Medical Device Manufacturer, devicelink.com.
"The Radio Pill", Rowlands, et al., British Communications and Electronics, Aug. 1960, pp. 598-601.
Video Camera to "TAKE"—RF System Lab, Dec. 25, 2001.
"Wellesley Company Sends Body Montiors into Space"—Crum, Boston Business Journal, 1998.
www.rfnorkia.com—NORIKA3, printed on Jan. 1, 2002.
"Wireless Transmission of a Color Television Moving Image from the Stomach using a Miniature CCD Camera, Light Source and Microwave Transmitter." Swain CP, Gong F, Mills TN. Gastrointest Endosc 1997;45:AB40, vol. 45, No. 4, 1997.
"In Pursuit of the Ultimate Lamp", Craford et al., Scientific American, Feb. 2001.
Manual of Photogrammetry, Thompson (Ed.), Third Edition, vol. Two, Copyright 1944, 1952, 1966 by the American Society of Photogrammetry.
www.jason.net/tinycam.htm, © 2001, printed Dec. 19, 2001.
www.middleeasthealthmag.com/article2.htm—Review proves the value of computers, © 2001, printed Nov. 29, 2001.
www.pedinc.com Personal electronic devices, © 1997.
BBC News Online—Pill camera to 'broadcast from the gut', Feb. 21, 2000, www.news.bbc.co.uk, printed Oct. 22, 2002.
High Throughput Microchannel DNA Sequencer, Balch, Human Genome Center. Biology and Biotechnology Research Program, Lawrence Livermore National Laboratory.
www.cartesian.com—Nanoliter quantitative aspiration and dispense (nQUAD) technology.
www.cartesiantech.com—Products for DNA microarray applications.
www.cartesiantech.com—Synchromizwd nQUAD technology.
www.mbt.washington.edu- Leroy Hood, Research Focus, Mar. 15, 2000.
Medical Diagnosis Reagents, vol. 16, pp. 88-107.
"Electroactive Polymer Actuators as Artificial Muscles", Y. Bar-Cohen, Ed., Spie Press, 2001.
"The 'Elephant Trunk' Manipulator, Design and Implementation", M.W. Hannan and I.D. Walker, pp. 1-6.
In vitro leucocyte adhesion to modified polyurethane sufaces—Bruil et al. Biomaterials 1992, vol. 13, No. 13, pp. 915-923.
What is Proteomics, Mar. 15, 2000.
International Search Report of International Application No. PCT/IL02/00041, dated Jul. 30, 2002.
"Robots for the Future"—Shin-ichi, et al. http://jin.jcic.or.jp/nipponaia13/sp05 html. printed Nov. 29, 2001.
Office Action for U.S. Appl. No. 10/036,490 mailed on Aug. 5, 2004.
Final Office Action for U.S. Appl. No. 10/036,490 mailed on May 12, 2005.
Office Action for U.S. Appl. No. 10/036,490 mailed on Sep. 20, 2005.

* cited by examiner

SYSTEM AND METHOD FOR IN-VIVO SAMPLING AND ANALYSIS

CROSS-REFERENCE TO RELATED APPLICATIONS

This application is a National Phase Application of PCT International Application No. PCT/IL03/00651, International Filing Date Aug. 7, 2003, which claims priority of US Provisional Patent Application, 60/402,703, filed Aug. 13, 2002, both of which being incorporated by reference herein in their entirety.

FIELD OF THE INVENTION

The present invention relates to the field of in vivo diagnostics. More specifically, the present invention relates to a system and method for in vivo and in-situ sampling and analysis of conditions prevailing in a body lumen.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Likewise, abnormalities in the physical conditions of the body, such as elevated temperature, may indicate pathology. Early detection, identification and location of abnormal conditions may be critical for correctly diagnosing and treating various pathologies.

Medical detection kits are usually based on in vitro testing of body fluid samples for the presence of a suspected substance. A known in vitro test is, for example, an agglutination test. Agglutination tests typically rely on the ability of an antibody to form large cross-linked antibody-antigen complexes that precipitate out of a solution. The process of agglutination normally includes 2 steps: sensitization (involves the attachment of antibodies (Ab) to antigens (Ag)) and lattice formation (cross lining between sensitized particles, which results in visual agglutination). Some factors can enhance these reactions, for example, pH, temperature, incubation time, ionic strength (salt concentration) of the suspending solution and so on.

Agglutination reactions, also referred to as the indirect Coombs test, usually involve the precipitation of cells. Frequently, indirect cross-linking is used to form the aggregation. A secondary antibody may be added that binds to the primary antibodies that have bound to their epitope on the surface of the cell. Another known group of agglutination tests are the Latex Agglutination Tests (LAT). These immunoassay tests have been in clinical use for more than 50 years. The tests are used to detect the presence of an antibody or antigen in a variety of in vitro samples of bodily fluids including saliva, urine, cerebrospinal fluid, gastrointestinal secretions or blood. Depending on the sample under investigation, and the specific substance one is looking for, either antibodies or antigens are attached to latex beads (typically, spherical beads). When the corresponding antigen or antibody is present, the latex beads agglutinate, i.e. clump together into visible particles, when mixed or come to contact with the sample. The latex beads may be replaced by other polymers such as polystyrene or even gold particles.

Agglutination tests are typically performed on glass slides, "cards" with depressions for adding Ag and Ab or tubes and strips on which the agglutination exposes the underlying colored markers.

In vitro testing of samples does not easily enable the localization or identification of the origin of an abnormally occurring substance. In many instances localizing an abnormally occurring substance in a body lumen greatly contributes to the identification of pathology, and the proper type of treatment and thus contributes to the facile treatment of the identified pathology. For example, bleeding in the stomach may indicate an ulcer while bleeding in the small intestine may indicate the presence of a tumor. The detection of some conditions in the GI tract, such as bleeding, is possible by endoscope. However, this possibility is limited to the upper or lower GI tract. Thus, conditions in other parts of the GI tract, such as the small intestine, are not easily detected by endoscopy.

There is therefore a need for a system and method that may enable the localization or identification of the origin of an abnormally occurring substance throughout body lumens.

SUMMARY OF THE INVENTION

There is thus provided, according to embodiments of the invention, a system and method for in vivo and in situ sampling and analyzing. According to one embodiment a system comprises an image sensor, an illumination source and agglutinative particles. According to another embodiment a system comprises an image sensor, an illumination source and a sample chamber that contains agglutinative particles. Typically, the agglutinative particles may be capable of adhering to an analyte, if it is present in a sample, such that clusters or precipitates of agglutinative particles and analytes are formed. An analyte may be a substance, such as a chemical or biological moiety, that is capable of adhering to an agglutinative particle. According to one embodiment clusters of agglutinative particles are discernible whereas agglutinative particles that are not clustered are typically indiscernible.

According to an embodiment of the invention a system comprising an image sensor, an illumination source and agglutinative particles, optionally contained within a sample chamber, is inserted in vivo and a body lumen sample, typically a fluid sample, is reacted with the agglutinative particles. According to one embodiment a sample is collected into the sample chamber. The sample chamber may be illuminated and imaged while in vivo. Agglutination, should it occur in the sample, can thus be observed in the images taken of the sample chamber, thereby providing indication of the presence of an analyte in the sample.

According to one embodiment there is provided an autonomous device designed to traverse the GI tract. The device includes at least one illumination source and at least one image sensor for obtaining images of the GI tract. The device, according to one embodiment, may include a transmitter for transmitting data (e.g., image data) to an external receiving system. According to one embodiment the device includes a sample chamber, which is typically positioned in the field of illumination and in the field of view of the image sensor. The chamber, at least portions of which may be transparent in the illumination wavelengths, is typically open to the body lumen environment for receiving samples from the body lumen environment. According to another embodiment the device comprises an optical window, typically for illuminating and imaging a body lumen through the window. The agglutinative particles may be immobilized to a chamber on the external surface of the optical window (the surface facing the body lumen environment), such that an optical change occurring due to agglutination may be imaged. Thus, images of a body lumen may contain additional information regarding the presence of analytes in the body lumen. Furthermore, the appearance of discernible agglutination, which indicates the presence of an analyte, in specific images, may be directly associated with a specific location within the body lumen as can be deduced from the images of the body lumen or by other localization methods.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

A system, according to embodiments of the invention, is typically designed to be inserted in and/or passed through a body lumen for sampling contents of the body lumen. A sample or samples may be collected into one or more sample chamber(s). The sample chamber, which typically contains agglutinative particles, may be illuminated and imaged while it is in a body lumen such that optically discernable indication of the presence of a specific analyte may show up in the images.

Figure 1:
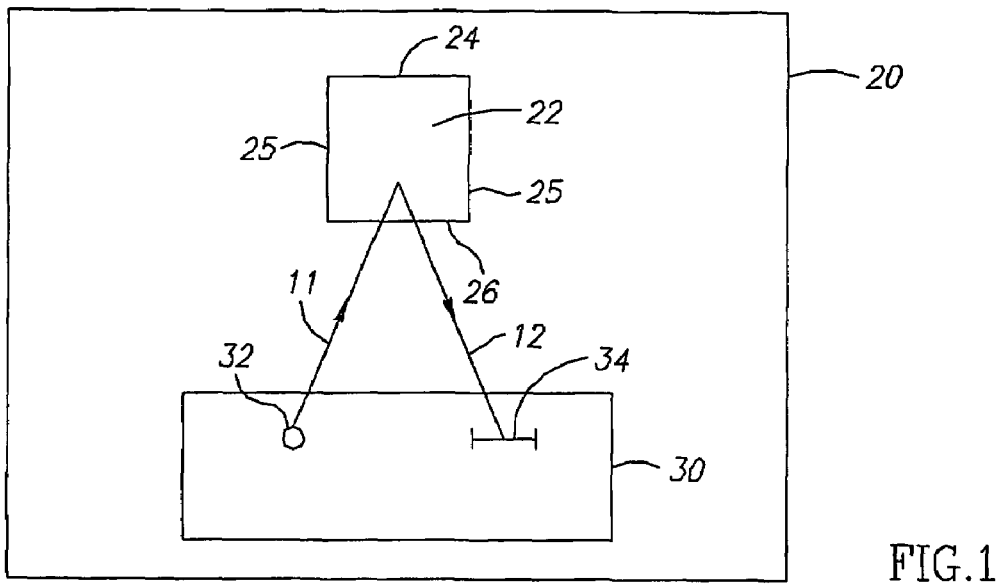
FIG. 1 is a schematic illustration of a system according to one embodiment of the invention.

An exemplary system, according to one embodiment of the invention, is illustrated in FIG. 1. The system 20 comprises a sample chamber 22, and an optical detecting unit, e.g., imaging system 30. Imaging system 30 comprises an illumination source 32 and an image sensor 34. The illumination source 32 may illuminate chamber 22 and may also illuminate a body lumen. The image sensor 34 may image chamber 22 and may also image the body lumen. The imaging system 30 may further comprise an optical system (not shown), which may include, for example, lenses and/or collimators for collecting reflected light and for focusing an image on the image sensor 34. According to other embodiments the system 20 may include a plurality of illumination sources and/or a plurality of image sensors. Image sensor 34 may be any sensor suitable for in vivo imaging, for example an imager, such as a CCD, CMOS imaging chip, photodiodes etc. The image sensor 34 may process the received light rays for example by forming an image of the chamber. The image may be stored in the imaging system 30 or may be further transmitted to an external receiving system. In alternate embodiments other optical detectors may be used for detecting agglutination in the chamber 22. Typically, agglutination may cause a change in the optical characteristics of a sample. For example, agglutination may cause a change of color, a change in the optical density, in scattering, transparency, and so on. A device suitable for receiving and processing light rays that have passed through chamber 22, such as a spectrophotometer, may be used, for example, to detect optical characteristics of a sample in the sample chamber 22.

Sample chamber 22, according to some embodiments, comprises a chamber cavity enclosed by two sides 25, a bottom 26 and a membrane 24, the membrane 24 typically constituting a partition between the body lumen environment and the chamber cavity. According to some embodiments at least the bottom 26 of the chamber 22 may be transparent in the wavelength of illumination. According to other embodiments one or two of the sides 25 are transparent in the illumination wavelength. According to yet other embodiments any of bottom 26 or sides 25 may comprise a reflecting surface, for example, for more effectively collecting reflected light. In this case, light rays traversing the chamber will be essentially all reflected back to the image sensor. In alternate embodiments chamber 22 may comprise other components and have other shapes, such as a sack-like, rectangular or cylindrical shape.

Chamber 22, which is typically configured for containing endo-luminal samples, such as body lumen fluids, may contain agglutinative particles, such that agglutination may occur in the sample chamber if the sample contains specific analytes (for example, as further detailed below).

When the system 20 is introduced into a body lumen the lumen environment is sampled. An endo-luminal sample may passively enter the chamber 22 through membrane 24. Alternatively, the sample may be actively drawn into the chamber, for example, based on osmotic pump technology, wherein flux of fluids into the chamber is typically a function of pore size and the outside to inside concentration gradient. Alternatively, the sampling can be periodic, controlled, for example, by a switch.

Membrane 24 of chamber 22 may be fabricated from any suitable material, for example from silicon materials, polysulphone, and more. According to one embodiment the membrane may have properties, such as hydrophilicity/hydrophobicity or the membrane may be charged to attract or repel certain analytes. According to another embodiment the membrane 24 is a semi-permeable membrane. According to one embodiment the membrane is permeable to relatively large molecules such as antibody complexes. According to other embodiments the membrane 24 may have any desired cut off size. For example, the cut off size may be compatible with the size of a suspected analyte or substance. Typically, membrane 24 may include a mesh having a pore size larger than the size of a suspected substance so as to enable the passing of the substance through the membrane into the chamber cavity. According to other embodiments the cut off size may be designed to retain the agglutinative particles within the chamber cavity. In alternate embodiments agglutinative particles may be immobilized in the chamber 22, such as by being immobilized to a chamber side or bottom or to an appendage that is restricted to the chamber. It should be appreciated by a person skilled in the art that the agglutinative particles, according to embodiments of the invention, require a certain amount of mobility in order to agglutinate. For example, agglutinative particles may be embedded in a gel that coats the inside of the chamber wall or bottom. In alternative embodiments the agglutinative particles may be held against a chamber side by electric charge attraction, or magnetic forces.

Imaging system 30 transmits and receives light to and from chamber 22. Chamber 22 may be illuminated by illumination source 32 such that optical changes, typically as a result of the interaction between agglutinative particles and analytes, which may occur in the chamber 22, may be detected by image sensor 34.

An optical change may include any change, typically in an in vivo sample, that may be detected by an optical detector, such as an image sensor. Examples of possible optical changes may include a change in color, hue, brightness, intensity, optical density, transparency, light scattering etc., or a combination of optical changes.

It will be appreciated that chamber 22 may be made of any suitable material such as plastic, glass etc. Parameters to be considered while assessing if a material is suitable may be, for example, the material's transparency, its safety for internal use, its durability under endo-luminal conditions and so on.

The system 20 may comprise one or more chambers such that the presence and/or concentration of one or more substances may be detected simultaneously or at different areas of the lumen.

The reaction between an agglutinative particle and an analyte may be reversible in which case the agglutinative particles may be used to detect a plurality of analyte sources, each source showing as a single event of an optical change. Also, the reaction kinetics may be such that the extent of the agglutination (which can be directly proportional to the intensity of the optical change) is proportional to the analyte concentration. According to certain embodiments a system may be calibrated for different agglutinative particles and analytes such that the concentration of an analyte in a sample may be deduced, as known in the art. For example, concentrations of analytes in agglutination reactions may be tested by a known system in which reactions are graded from 0 to 4 as follows: 0=no agglutination; 1+=barely detectable agglutination; 2+=agglutination with 50% clearing; 3+=agglutination with 75% clearing; 4+=visible cluster with suspending fluid totally cleared. In order to evaluate accurately the actual concentration of the analyte in the sample, a series of dilutions is made and the "titer" is determined, wherein titer is the reciprocal of the highest dilution giving any positive reaction. Alternatively, samples may be graded by an internal calibration system provided, for example, in one or more chambers in system 20.

The system, according to embodiments of the invention may thus enable to deduce not only the presence of a specific analyte at a specific in vivo location, but also its concentration at that location. Alternatively, particles specific for different analytes may be mixed or placed in separate chambers. Chamber 22 is illuminated by illumination source 32 which may be any illumination source compatible with chamber 22 and image sensor 34. Light sources such as light emitting diodes (LEDs) can be used. Optionally, a collimator or reflector (not shown) may be used for collecting/directing light rays from the illumination source 32 to chamber 22 and through them to the image sensor 34.

According to one embodiment the system 20 may be set up such that illumination source 32 and image sensor 34 are in front of chamber 22 such that light transmitted from illumination source 32 transmits through the transparent bottom 26 of chamber 22 and is reflected to image sensor 34. According to one embodiment light rays (represented by arrow 11) are emitted from the illumination source 32 and are directed at the transparent bottom 26 of chamber 22. The light rays (represented by arrow 11) pass through the transparent bottom 26, and according to one embodiment, may heat the sample. Light rays (represented by arrow 12) reflected from the chamber 22 are received on the image sensor 34. Alternatively, the system 20 may be set up such that chamber 22 is positioned in between an illumination source 32 on one side and an image sensor 34 on the other (not shown).

Differently designed components and differently set up systems may also be utilized according to embodiments of the invention. For example, the system 20 may include a chamber or plurality of chambers that do not have a membrane but rather each chamber comprises two openings to allow collecting and discharge and replacement of the sample in the chamber as the system samples new areas of the body lumen environment. According to some embodiments the chambers may be formed as capillaries etched, for example, into a slab of glass, or formed in between two glass slabs one of which contains preformed slots or channels.

The components of the system according to embodiments of the invention may be specifically designed for the system, or the system may utilize some components from other systems that operate in body lumens, thus economically taking advantage of existing components. For example, the system of the invention may be incorporated into or affixed onto medical devices meant for being inserted into body lumens, such as needles, stents, endoscopes, catheters or capsules that can pass through the GI tract. Endoscopes utilize a light source and sometimes an imaging device while operating. Thus, the system of the invention can be incorporated into a suitable medical device, such as an endoscope, and utilize the device's light source and imaging device for detecting the presence and/or concentration of analytes.

Figures 2A, 2B:
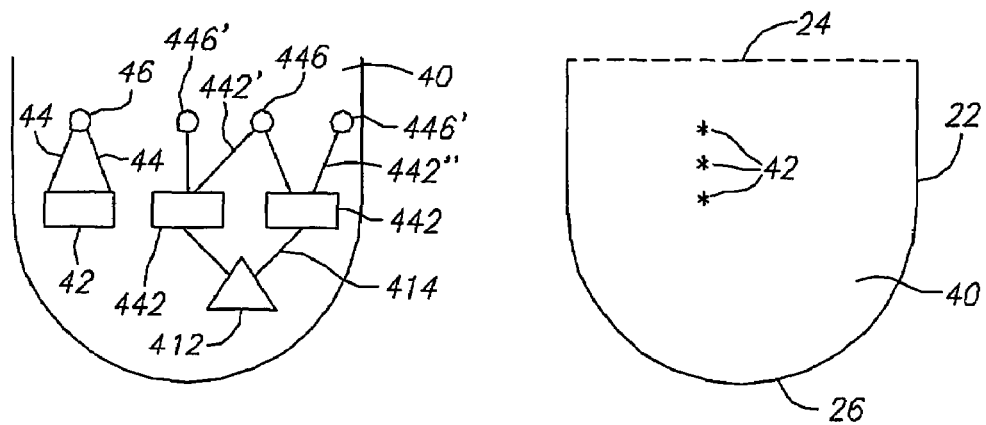
FIG. 2A is a schematic illustration of agglutinative particles in accordance with an embodiment of the invention.
FIGS. 2B-E schematically illustrate a chamber including agglutinative particles in accordance with embodiments of the invention.

Reference is now made to FIG. 2A, which illustrates agglutinative particles according to an embodiment of the invention. Agglutinative particles, according to one embodiment are capable of aggregating analytes, typically by adhering to an analyte and/or by cross linking to other particles. Typically an agglutinative particle includes a microscopic particle which is coated with (or otherwise adhered to) typically chemical or biological molecules such as antibodies (Ab) or antigens (Ag). According to one embodiment microscopic particles may be latex or magnetic particles. According to one embodiment agglutinative particles may include primary and secondary Abs such as homo-specific Abs or monoclonal Abs. Typically, antibodies may recognize and agglutinate antigenic determinants that may be present in a sample. For example, tumor antigens are expected to be found in a higher concentration in the vicinity of a tumor than in remote areas or in the blood stream. Thus, antibodies that may recognize and agglutinate in the presence of tumor antigens may additionally contribute to the diagnosis by enabling the localization of these tumor antigens, as further described in the specification. The localization may be important for an accurate diagnosis as most known GI tumor antigenic markers are not specific to a single tumor type and may represent, for example gastric, pancreatic and colon tumors.

According to other embodiments agglutinative particles may include antigenic determinants or epitopes that may be recognized by antibodies present in a sample. According to yet further embodiments agglutinative particles may include a particle having linkers attached to it, for binding an analyte and/or for binding another particle. According to other embodiments agglutinative particles may include Ab or Ag that are chemically attached to particles, such as to latex or magnetic particles. In yet other embodiments Ab or Ag are attached to specially shaped particles, optionally, to enhance sensitivity of the reaction (for example, by avoiding steric hindrance of the binding process). In other embodiments the agglutinative particles may include cells, such as bacteria (e.g., *H. pylori*). According to additional embodiments, any combination of agglutinative particles may be used. Correspondingly, an analyte may include an antigenic determinant, such as antigen bearing cells, for example, cancerous cells, viruses, bacteria, fungi and other parasites etc. Alternatively, an analyte may be an antibody that is present in a body lumen, such as antibodies produced in response to a viral or bacterial attack or in response to the presence of a tumor or other pathologies. An analyte may further include substances, such as chemical or biological determinants having affinity to agglutinative particles.

According to one embodiment, in sample 40 an analyte 46 may bind to a particle 42 through linkers 44 that are attached to particles 42. Linkers 44 may include, for example, Morphollno ethane sulphonic acid available as MES/Protein Solution (by Merk or Sigma) or WSC: 1-(3-dimethylaminoprophyl)-3-ethylcarbdlimide (by Aldrich-Sigma). Particles with linkers may include, for example, OptiBind™ Polysterene microparticles or OptiLink™ Carboxylate-Modified Microparticles.

According to some embodiments analyte 446, which may be an antigen, may agglutinate particles, for example, by binding to one arm 442' of Ab 442 wherein another arm 442" of Ab 442 is bound by another analyte particle (for purposes of illustration 446'). Thus, when an analyte (such as 446 and 446') is present in a sample 40 particles, such as particles which include Ab 442 will agglutinate, typically forming a visible structure.

According to some embodiments, a secondary particle 412 having arms 414 may be present in the sample to ensure cross linking of Ab 442. Typically, binding of Ab 442 to an analyte may cause a change in the Ab (e.g., a chemical or a configuration change). Secondary particle 412 will bind to Ab 442 only in the Ab's bound configuration (i.e., when Ab 442 is bound to an analyte). Thus, agglutination of Ab 442 by secondary particles 412, which will occur only in the presence of an analyte (e.g., 446 and 446'), may enhance formation of visible structures.

Agglutinative particles 42, Ab 442 and/or secondary particles 412 may be colored. According to one embodiment, agglutinative particles (such as agglutinative particles 42, Ab 442 and/or secondary particles 412) may have different shapes and may have a diameter in the range of 0.1 to 300 micron; other diameters are also possible. Typically, the agglutinative particles are indiscernible when they are dispersed in a sample, however, when agglutination occurs, the gathering or precipitate of the particles becomes discernable. According to one embodiment the agglutinative particle 42 or the Ab 442 are colored such that when agglutination occurs a color becomes visible in the sample. Typically, light absorption and scattering may be dependent on particle size together with wavelength of illumination and relative viewing angle and therefore changes in light absorption and/or scattering with agglutination, may follow generally known functions. According to another embodiment the secondary particle 412 is colored such that when agglutination occurs a color becomes visible in the sample. According to yet another embodiment an optically discernable reaction (such as a clouding or a color reaction) occurs once an agglutinative particle binds, or is bound by an analyte. This optical reaction may typically be discernable only when agglutination occurs. For example, precipitates or conglomerates may become visible when they a large enough. Alternatively, large particles may cease to scatter light effectively relatively to smaller particles. It should be appreciated by a person skilled in the art that although the analyte illustrated in FIG. 2A is an antigen and the agglutinative particle illustrated in FIG. 2A includes an antibody, the analyte may be an antibody or any other suitable particle or substance and the agglutinative particle may include an antigen or any other suitable particle or substance.

Figure 2C:
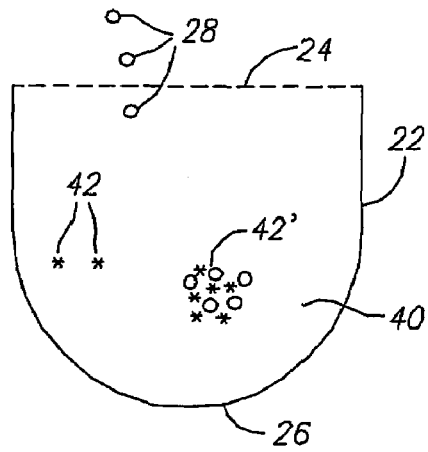
Figure 2D:
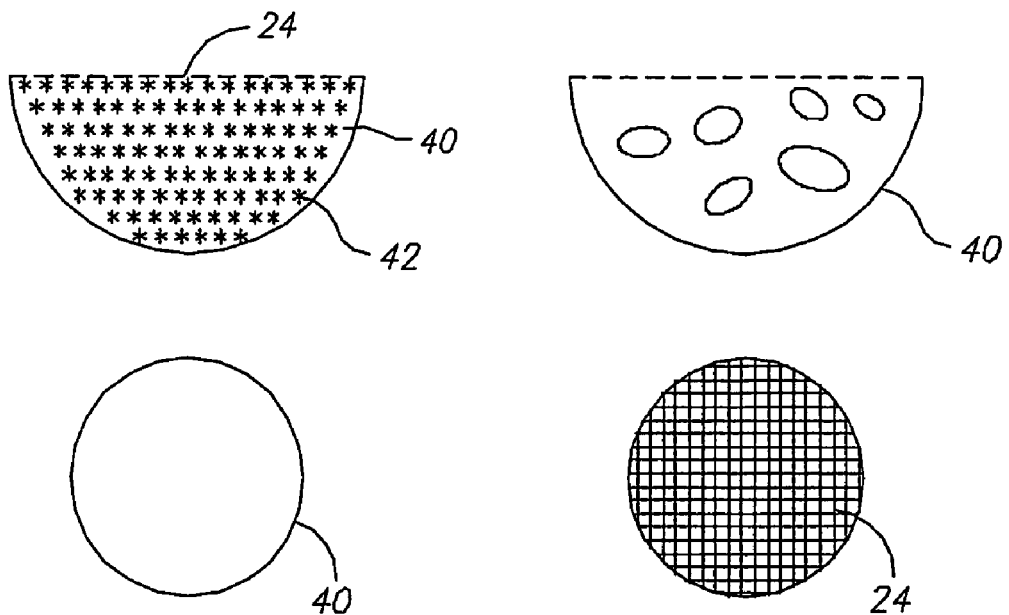
Figure 2E:
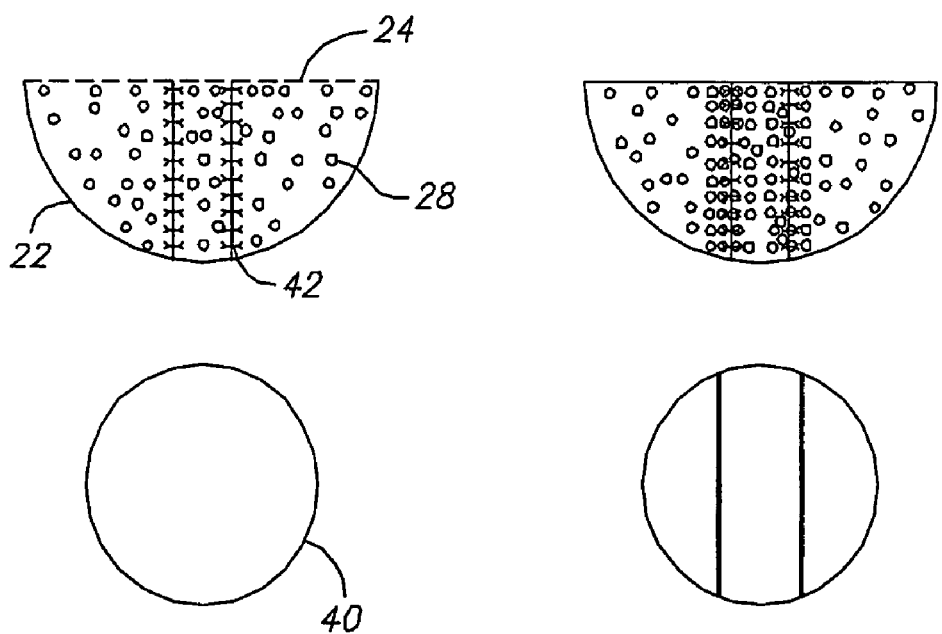

Reference is now made to FIGS. 2B-E illustrating a sample chamber including agglutinative particles in which the sample does not contain an analyte suitable for reacting with the agglutinative particles (e.g., FIG. 2B) and a sample chamber including agglutinative particles in which the sample contains an analyte suitable for reacting with the agglutinative particles (e.g., FIG. 2C), according to embodiments of the invention. FIGS. 2D and 2E show a chamber including agglutinative particles in which the sample contains an analyte suitable for reacting with the agglutinative particles, before and after agglutination, according to embodiments of the invention. Chamber 22 may be incorporated in a device that is capable of being inserted into and passing through body lumens, such as the GI tract, blood vessels, the reproductive tract, the urinary tract etc. For example, the chamber 22 may be incorporated in a swallowbale capsule, as will be described below.

According to one embodiment sample chamber 22 includes a membrane 24 and a bottom wall 26 that may be at least partially transparent. In one embodiment the membrane 24 has a mesh size which allows an analyte 28 enter the chamber but does not allow agglutinative particles 42 exit the chamber. In one embodiment the membrane cut off size is in the range of 0.05 to 10 microns. Antibodies typically range in size between 100 Å to 200 Å, thus they may penetrate through membrane 24 while other particles, such as particles 42, having a size in the range of 0.1 to 300 microns are entrapped in the chamber 22. FIG. 2B illustrates a sample chamber 22 containing a sample 40 that does not have an analyte present in the sample. In this case particles 42 are randomly dispersed in sample 40 and are typically indiscernible. FIG. 2C illustrates a sample chamber 22 containing a sample 40 having an analyte 28 present in the sample. Sample 40 including the analyte 28 may flow through membrane 24 into chamber 22 from a body lumen environment. The presence of an analyte in sample 40 causes agglutination of particles 42 (such as described above) and a colored (or otherwise discernible) precipitate 42' becomes discernible. Alternatively, sample 40 may become cloudy or clear or may go through any other optical change following agglutination. As discussed above, the intensity of the optical change may indicate the concentration of an analyte. In an alternate embodiment, for example as illustrated in FIG. 2D, membrane 24 may be colored or contain visible marks. Agglutinative particles 42 are present in such a concentration so as to render sample 40 cloudy or otherwise obscure when they are randomly dispersed in the sample 40 (e.g., top left corner of FIG. 2D and in an overview, bottom left corner of FIG. 2D). However, if sample 40 contains an analyte the particles 42 will agglutinate (e.g., top right corner of FIG. 2D), the cloudiness of the sample 40 will be alleviated due to the agglutination and the membrane 24 may be exposed. The appearance of a visible membrane (e.g., as illustrated in the bottom left corner of FIG. 2D) 24 indicates that there is an analyte in the sample 40

According to another embodiment, exemplified in FIG. 2E, agglutinative particles 42 are immobilized within a sample chamber 22 (e.g., in two lines as illustrated in the top left corner of FIG. 2E). Before agglutination sample 40 may seem clear, cloudy or otherwise obscure (illustrated, for example, as an overview in the bottom left corner of FIG. 2E). After agglutination occurs, analyte 28, which is present in sample 40, agglutinates according to the immobilized agglutinative particles 42, e.g., in two lines (top right corner of FIG. 2E). An overview of the visible agglutination is illustrated in the bottom right corner of FIG. 2E.

Figure 3:
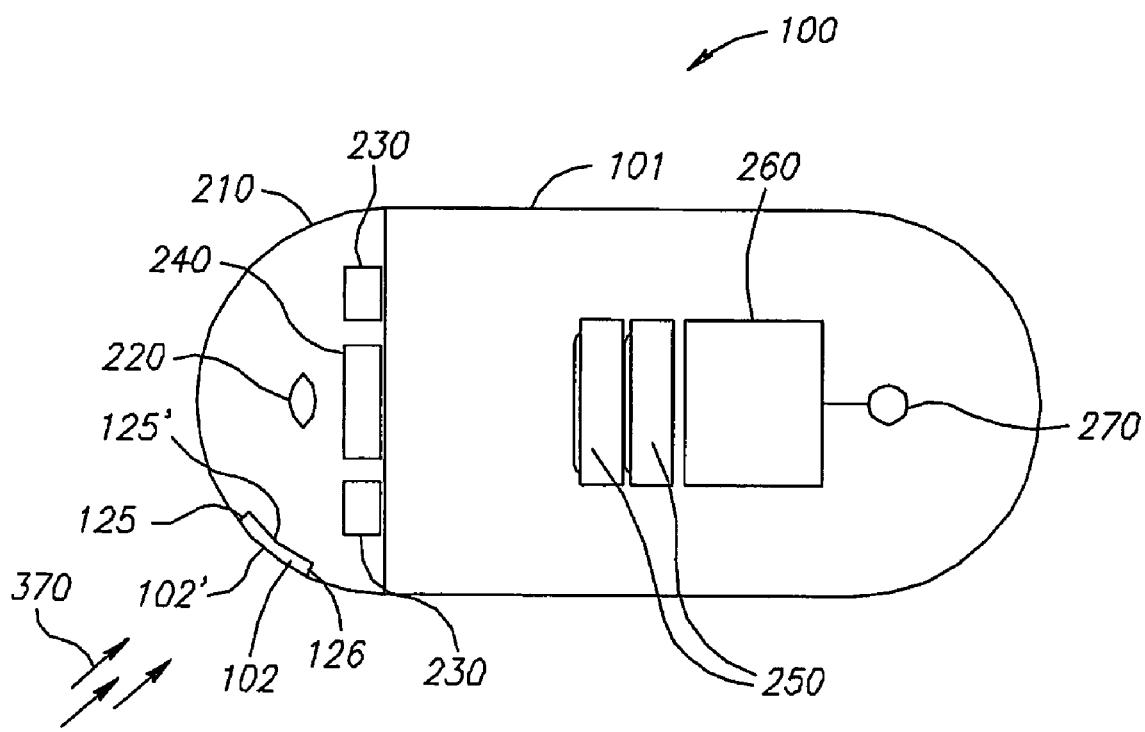
FIG. 3 is a schematic illustration of an in vivo imaging device according to an embodiment of the invention.

Reference is now made to FIG. 3, which schematically illustrates a device comprising a system, according to embodiments of the invention. According to one embodiment the device 100 is capable of being inserted into and passing autonomously through body lumens, such as the GI tract.

The device 100 typically comprises a shell 101 which may include an optical window 210. The device 100 further includes an imaging system, which comprises an illumination unit 230 and an image sensor 240. According to one embodiment the device 100 includes at least one sampling chamber 102. The sampling chamber 102' is typically positioned in the field of illumination and in the field of view of the image sensor 240. According to some embodiments a sampling chamber 102 may be integrated into the device shell 101, optionally in the optical window 210. According to other embodiments the device 100 does not include a sample chamber, rather agglutinative particles may be embedded in a medium which may be attached onto the optical window 210, such that the agglutinative particles may be in contact with a body lumen environment and may move through the medium to form visible formations (for example a strip of gelatin having agglutinative particles embedded within may be attached to the optical window external surface).

The imaging system may obtain images from inside a body cavity or lumen, such as the GI tract. The imaging system also obtains images of the sampling chamber 102, such that, according to an embodiment of the invention, a single image (frame) may contain image data of the body lumen and image data of the agglutination.

The illumination unit 230 may include one or more discrete light sources or may include only one light source. The one or more light sources may be a planar light source, a white light emitting diode (LED), or any other suitable light source, known in the art. Optimal parameters may be chosen for a light source while taking into account, for example, the scattering of light, which is a function of the relationship between the wavelength and particle size. The device 100 includes an image sensor 240, which acquires the images and an optical system 220 which focuses the images onto the image sensor 240. The image sensor 240 may be any suitable in vivo imager, such as a CCD or CMOS image sensor. The optical system 220 may include optical elements, such as one or more lenses (not shown), one or more composite lens assemblies (not shown), one or more suitable optical filters (not shown), or any other suitable optical elements (not shown) adapted for focusing an image on the imaging sensor. According to one embodiment the illumination unit 230 illuminates the sampling chamber 102 and inner portions of the body lumen through the optical window 210. In an embodiment of the invention the device 100 may comprise a plurality of imaging devices and, optionally, their corresponding optical systems, and optionally a plurality of illumination sources. For example, a plurality of imaging devices and optionally a plurality of interaction chambers may be positioned at opposing sides of the device for multi-directional sampling and/or viewing of the body lumen. Device 100 further includes a transmitter 260 and an antenna 270 for transmitting data, e.g., image signals of the image sensor 240, and one or more power sources 250. The power source(s) 250 may be any suitable power sources such as but not limited to silver oxide batteries, lithium batteries, or other electrochemical cells having a high energy density, or the like. The power source(s) 250 may provide power to the electrical elements of the device 100. It is noted that for the sake of clarity of illustration, the connections between the power source 250 and the circuits or components of the device 100 which receive power therefrom, are not shown in detail.

According to one embodiment, as the device 100 is transported through the body lumen, such as the gastrointestinal (GI) tract, the imager acquires images (frames), which are processed and transmitted to an external receiver/recorder (not shown) worn by the patient for recording and storage. The recorded data may then be downloaded from the receiver/recorder to a computer or workstation (not shown) for display and analysis. Other systems and methods may also be suitable.

During the movement of the device 100 through the GI tract, the imager may acquire frames at a fixed or at a variable frame acquisition rate. For example, the imager may acquire images at a fixed rate of two frames per second (2 Hz). However, other different frame rates may also be used, depending, inter alia, on the type and characteristics of the specific imager or camera or sensor array implementation that is used, and on the available transmission bandwidth of the transmitter 260. The downloaded images may be displayed by the workstation by replaying them at a desired frame rate. This way, the expert or physician examining the data is provided with a movie-like video playback, which may enable the physician to review the passage of the device through the GI tract and to observe occurrences of agglutination.

The device 100 may be constructed as an ingestible video capsule, similarly to capsules disclosed in U.S. Pat. No. 5,604,531 to Iddan et al., WO 01/65995 to Glukhovsky et al., U.S. Pat. No. 6,240,312, to Alfano, or in WO 01/50941 to (all of which are incorporated herein by reference). A capsule optionally utilized according to another embodiment of the invention may be a remote-controllable, micro-scale device having a motion mechanism, such as a mechanical propeller that may be driven by an electric motor or may be turned by a build in gas flow. Another capsule may contain a rotation mechanism that can be charged by external radio waves and that can initiate capsule rotation. In alternate embodiments the system and method may be used in conjunction with other in-vivo devices, such as endoscopes, catheters, needles, stents and the like.

According to one embodiment the chamber 102 is open to the GI tract environment, such that GI tract fluids 370 can enter the chamber 102, typically through a membrane 102', either passively or actively as described above. The agglutinative particles (not shown) contained within the chamber 102 are typically restricted to the chamber. The particles may be unable to leave the chamber because of the membrane 102' which enables the entrance of GI tract fluids 370 but does not allow leakage of the particles from the chamber. According to one embodiment the chamber 102 comprises sides 125 and 125' and bottom 126. Typically, chamber 102 may be at least partially transparent to enable viewing optical changes within the chamber. According to one embodiment side 125' is transparent so as to allow illumination from the illumination unit 230 enter the chamber for illuminating the sample. According to one embodiment side 125 and/or bottom 126 may be coated by a reflecting surface, for example, a mirror, for more effectively collecting reflected light and for possibly enhancing the image of the sample chamber 102. The reflective surface may have a color contrasting that of the particles.

According to one embodiment device 100 schematically shown in FIG. 3 is designed to be inserted into the GI tract and pass through the entire tract. However, the device 100 is not limited to any specific configuration. For example, in accordance with the specific imager and specific energy requirements, device elements (such as the illumination source and transmitter) may be connected by cable to an external power supply or to an external receiving system. Alternatively, the device may be powered externally (e.g., by an external electromagnetic field that may induce power in a set of coils which may be included in the device 100). Further, the device may be of any shape suitable for being inserted into a body lumen and for passing through the body lumen or for being included in a device that is inserted into a body lumen.

According to one embodiment, as the device 100 proceeds down the GI tract, minute amounts of GI tract fluids 370 may slowly enter the chamber 102. Optionally, GI tract fluids that enter the chamber 102 in one area of the GI tract may be displaced by fluids from a newly reached area in the GI tract. According to some embodiments the device 100 constantly samples the GI tract environment throughout the lumen. Thus, the origin or location of pathologies in the GI tract can be detected. For example, the presence of a tumor or tumor cells in a patient's GI tract can be detected by inserting a device according to an embodiment of the invention into the patient's GI tract. The device may comprise a sample chamber, which includes, for example, agglutinative particles that may specifically bind to tumor cells. For example, CAM 17.1, which is an anti-mucin monoclonal antibody and which has recently been proven as a reagent for serological diagnosis of pancreatic cancer and has been shown to bind to a sialic-acid-containing determinant of mucin, which is an epitope that shows wide distribution throughout the gastro-intestinal tract (Eclleston D W, Milton J D, Hoffman J, Bara J, Rhodes J M, *Digestion*. 1998 November-December; 59(6):665-70). Another example of a suitable agglutination assay may be the Ca 19-9 Agglutination Assay in which 116-NS-19-9 is monoclonal antibody generated against a colon carcinoma cell line in order to detect a monosialoganglioside (CA19-9) found in patients with gastrointestinal adenocarcinoma.

The device 100 passively travels through the patient's GI tract imaging both the GI tract and the sample chamber. A location of a tumor in the GI tract may be characterized by the presence of antibodies such as mentioned above. GI tract fluids sampled at the location of the tumor will typically contain the antibodies. The antibodies react with the agglutinative particles such that agglutination occurs in the sample chamber. The agglutination, typically resulting in an optical change, may be imaged by the image sensor 240. The image of the optical change and of the location in the GI tract may be transmitted to an external operator who may identify the location of the device 100 at the time the image was produced and thus identify the origin of the tumor.

Figure 4:
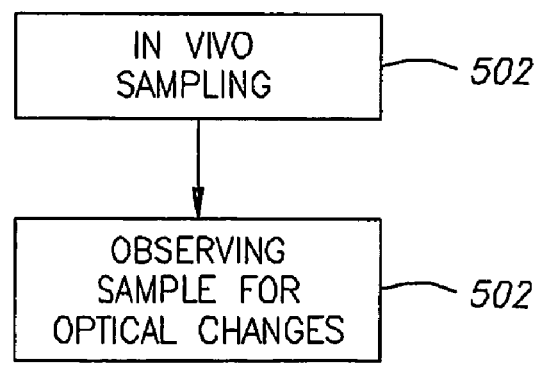
FIG. 4 is a box diagram illustrating a method for in vivo sampling and analyzing, according to an embodiment of the invention.

Reference is now made to FIG. 4 which is a box diagram illustrating a method for in vivo sampling and analyzing, according to an embodiment of the invention. According to one embodiment a body lumen environment is sampled, in vivo, in the presence of agglutinative particles (502), for example, a sample of a body lumen may be combined with agglutinative particles. According to one embodiment the sample and agglutinative particles are combined within a chamber. The sample is observed, in vivo, for optical changes (504). Typically, the step of observing the sample includes detecting at least one optical change within the combined sample. According to one embodiment the step of detecting an optical change is done by imaging the combined sample. Optionally, images of the sample may be transmitted to an external receiving unit. According to one embodiment the method further includes the step of obtaining images of the body lumen.

It will be appreciated by persons skilled in the art that the present invention is not limited to what has been particularly shown and described hereinabove. Rather the scope of the present invention is defined only by the claims, which follow:

The invention claimed is:

1. An ingestible capsule comprising:
   an optical window, said window having immobilized thereto agglutinative particles capable of interacting with at least one analyte and further capable of gathering into agglutination groups so as to cause an optical change;
   at least one imaging system configured for detecting at least the optical change; and
   a transmitter configured for transmitting image data to an external receiving system.

2. The system according to claim 1 comprising at least one illumination source.

3. The system according to claim 1 wherein the imaging system is configured for imaging a body lumen.

4. The system according to claim 1 wherein the agglutinative particles include at least one molecule selected from the group consisting of: antibodies, antigens, cells and linkers.

5. The system according to claim 1 wherein the optical change is selected from the group consisting of: a change of color, a change of hue, a change of brightness, a change of intensity, a change of optical density, a change of transparency, a change of light scattering and any combination thereof.

6. The system according to claim 1 wherein the in vivo imaging system includes at least a photodiode, a CCD or a CMOS.

7. The device according to claim 1 comprising at least one chamber, said chamber configured for containing the agglutinative particles and an in vivo sample.

8. The system according to claim 7 wherein the chamber is at least partially transparent.

9. The system according to claim 7 wherein the imaging system is configured for imaging the chamber.

10. The system according to claim 7 wherein the at least one analyte is in the in vivo sample.

11. A method for in vivo analysis, the method comprising the steps of:
    obtaining a sample from a body lumen;
    combining in vivo the sample with agglutinative particles capable of interacting with at least one analyte in the sample and gathering into agglutination groups; and
    detecting at least one optical change upon formation of the agglutination groups.

12. The method according to claim 11 wherein the step of detecting at least one optical change includes imaging the combined sample.

13. The method according to claim 11 comprising the step of obtaining at least one image of the body lumen.

14. The method according to claim 11 comprising transmitting data to an external receiving unit.

15. The method according to claim 11 further comprising the step of ingesting a capsule comprising the agglutinative particles, wherein said step of obtaining a sample is performed using the capsule.

16. The method according to claim 11 further comprising the step of identifying a location of the combined sample within the body lumen.

17. The method according to claim 11, wherein the combined sample and agglutinative particles gather into the agglutinative groups proportional to the concentration of analyte in the sample.

* * * * *